(12) United States Patent
Furuta et al.

(10) Patent No.: US 9,891,214 B2
(45) Date of Patent: Feb. 13, 2018

(54) IMMUNOLOGICAL ASSAY METHOD

(75) Inventors: Yuki Furuta, Ayase (JP); Koji Shintani, Ayase (JP)

(73) Assignee: TOSOH CORPORATION, Shunan-shi, Yamaguchi (JP)

( * ) Notice: Subject to any disclaimer, the term of this patent is extended or adjusted under 35 U.S.C. 154(b) by 496 days.

(21) Appl. No.: 13/997,835

(22) PCT Filed: Dec. 27, 2011

(86) PCT No.: PCT/JP2011/007315
§ 371 (c)(1),
(2), (4) Date: Jul. 17, 2013

(87) PCT Pub. No.: WO2012/090493
PCT Pub. Date: Jul. 5, 2012

(65) Prior Publication Data
US 2013/0288390 A1 Oct. 31, 2013

(30) Foreign Application Priority Data

Dec. 28, 2010 (JP) ................................ 2010-294126
Dec. 19, 2011 (JP) ................................ 2011-277597

(51) Int. Cl.
*G01N 33/543* (2006.01)

(52) U.S. Cl.
CPC ..... *G01N 33/543* (2013.01); *G01N 33/54306* (2013.01)

(58) Field of Classification Search
CPC .............................................. G01N 33/54306
USPC .................................................. 436/518, 501
See application file for complete search history.

(56) References Cited

U.S. PATENT DOCUMENTS

| 4,434,236 | A | * | 2/1984 | Freytag | ............................. 435/5 |
| 5,089,391 | A | * | 2/1992 | Buechler | ................ G01N 33/53 435/7.1 |
| 5,696,264 | A | * | 12/1997 | Albarella | ............. C07D 475/04 544/257 |
| 5,858,803 | A | | 1/1999 | Schenk et al. | |
| 6,063,581 | A | | 5/2000 | Sundrehagen | |
| 6,436,658 | B1 | | 8/2002 | Seman | |
| 2001/0006775 | A1 | | 7/2001 | Oku et al. | |
| 2002/0015968 | A1 | | 2/2002 | Ferguson et al. | |
| 2005/0009128 | A1 | | 1/2005 | Yuan et al. | |
| 2006/0172362 | A1 | | 8/2006 | Yuan et al. | |
| 2008/0305507 | A1 | | 12/2008 | Yuan et al. | |

FOREIGN PATENT DOCUMENTS

| EP | 0177191 B1 | * | 11/1990 |
| EP | 0 411 945 A2 | | 2/1991 |
| JP | 10-253632 A | | 9/1998 |
| JP | 2870704 B2 | | 3/1999 |
| JP | 2002-529102 A | | 9/2002 |
| JP | 2007-85779 A | | 4/2007 |
| JP | 2007-528714 A | | 10/2007 |

OTHER PUBLICATIONS

Graves et al. "A Universal competitive fluorescence polarization activity assay for S-adenosylmethionine utilizing methyltransferases" Analytical Biochemistry 373 (2008) 296-306.*
Lermo, A. et al., "Immunoassay for folic acid detection in vitamin-fortified milk based on electrochemical magneto sensors", Biosensors and Bioelectronics 24 (2009) pp. 2057-2063.
Extended European Search Report dated Oct. 10, 2014 issued in application No. 11852495.8-1408.
English Translation of International Preliminary Report on Patentability issued in PCT/JP2011/007315 dated Jul. 2013.
Nadezhda Doncheva et al., "Study of Homocysteine Concentration in Coronary Heart Disease Patients and Comparison of Two Determination Methods", Annals of Nutrition & Metabolism, 2007, pp. 82-87, vol. 51, No. 1.
Communication, dated Oct. 7, 2016, issued by the European Patent Office in counterpart European Patent Application No. 11852495.8.
Golden et al., "A portable array biosensor for food safety," *Proc. of SPIE*, 2004, vol. 5587, pp. 241-244.

* cited by examiner

*Primary Examiner* — Lisa V Cook
(74) *Attorney, Agent, or Firm* — Sughrue Mion, PLLC

(57) ABSTRACT

[Problem] To provide a so-called competitive immunological assay method capable of more uniformly immobilizing on a solid phase a substance equivalent to an antigen. [Solution] This immunological assay method measures an analyte substance in a sample by using: an equivalent substance immobilized on the solid phase during the execution of the assay, the equivalent substance being immunologically equivalent to the analyte substance; and a labeled antibody for specifically binding to the substance equivalent to the analyte substance. The assay method is characterized in that the equivalent substance is immobilized on the solid phase using: a bond between the equivalent substance and a carrier substance, the carrier substance being a substance to which the labeled antibody does not bind; and a bond between the carrier substance and a specific binding substance immobilized on the solid phase, the specific binding substance being a substance that binds specifically to the carrier substance.

6 Claims, No Drawings

IMMUNOLOGICAL ASSAY METHOD

CROSS REFERENCE TO RELATED APPLICATIONS

This application is a National Stage of International Application No. PCT/JP2011/007315 filed Dec. 27, 2011, claiming priority based on Japanese Patent Application Nos. 2010-294126 filed Dec. 28, 2010 and 2011-277597 filed Dec. 19, 2011, the contents of all of which are incorporated herein by reference in their entirety.

FIELD

The present invention relates to an immunological assay method for measuring an analyte substance in a sample using: an equivalent substance which is immunologically equivalent to the analyte substance and is immobilized on (bound to) a solid phase during the execution of the measurement; and a labeled antibody which specifically binds to the analyte substance and the equivalent substance.

BACKGROUND

Specific substances present in the blood may be associated with specific diseases. For example, high levels or low levels of the specific substances out of a certain range may indicate development or seriousness of the specific diseases, and therefore such substances have been intensively measured in the field of clinical diagnosis.

There is homocysteine measurement in the blood, for example. Homocysteine is one of intermediate substances produced in the process of methionine metabolism in the body. Produced homocysteine is quickly metabolized through either of the pathways; conversion into methionine, or conversion into cysteine via cystathionine formation. High levels of homocysteine are considered as one of risk factors for cardiovascular disorders and thus the measurement thereof has attracted attention.

Immunological assay method is known as a method for measuring substances such as proteins, steroids, vitamins, and other immunologically antigenic substances (substances capable of artificially producing antibodies against the substances) in the blood. As the immunological assay method for homocysteine (Patent Literature 1), what is called a competitive assay method has been known. In the competitive assay method, the blood is used as a sample and homocysteine bound to the component in the blood by the S—S bond is first released. And next, homocysteine is converted into S-adenosylhomocysteine which is an immunologically measurable derivative, by addition of adenosine with the enzyme. Subsequently, this S-adenosylhomocysteine is competitively bound to a labeled anti-S-adenosylhomocysteine antibody with S-adenosylhomocysteine which was prepared in advance and immobilized on a water-insoluble solid phase. Next, homocysteine was measured by measurement of the amount of the labeled antibody bound to the solid phase after what is called a B/F (bound/free) separation procedure.

CITATION LIST

Patent Literature

Patent Literature 1: Japanese Patent No. 2870704

SUMMARY

Technical Problem

In the immunological assay method for homocysteine described in Patent Document 1, the water-insoluble solid phase with S-adenosylhomocysteine immobilized thereon was used. S-adenosylhomocysteine has been generally immobilized on (bound to) the solid phase by: binding S-adenosylhomocysteine to a carrier substance such as bovine serum albumin; and making the carrier substance in this obtained complex to be physically adsorbed to the solid phase. However, it has been difficult to uniformly immobilize (bind) S-adenosylhomocysteine to the solid phase with such immobilization. Therefore, the amount of S-adenosylhomocysteine bound to the solid phase easily varies. The measured results vary as the amount of S-adenosylhomocysteine bound to the solid phase varies, thereby causing lower reproducibility in some cases. When the amount of S-adenosylhomocysteine bound to the solid phase is intended to be controlled in order to avoid lower reproducibility, there has been a problem of complicated steps for quality control in preparation of the solid phase.

Further, there has been also a problem that some of S-adenosylhomocysteine is not involved in the immunoreaction with the antibody because of the binding to the carrier substance (for example, enclosed in the carrier substance), thereby hindering efficient immunoreaction with anti-S-adenosylhomocysteine labeled antibody. Such a problem may result in lower reproducibility. When this is intended to be avoided, there has been also a problem that a monoclonal antibody or the like whose immunoreaction is not hindered by the binding between S-adenosylhomocysteine and the carrier substance must be used as the anti-S-adenosylhomocysteine labeled antibody.

Although the immunological assay for homocysteine is described above as a specific example, the above-mentioned problems are common problems in terms of an immunological assay method for measuring an analyte substance using: an equivalent substance which is immunologically equivalent to the analyte substance and is immobilized on a solid phase; and a labeled antibody which specifically binds to the analyte substance and the equivalent substance, and in particular, a method in which the equivalent substance is used with a carrier substance being physically adsorbed to the solid phase while the equivalent substance is bound to the carrier substance for immobilizing it on the solid phase.

Solution to Problem

The present inventors have intensively studied to solve the above-mentioned problems found in the conventional technique and completed the present invention.

The present invention to solve the above-mentioned problems is an immunological assay method, comprising:

measuring an analyte substance in a sample by using: an equivalent substance which is immunologically equivalent to the analyte substance and immobilized on a solid phase during the execution of the measurement; and a labeled antibody which specifically binds to the analyte substance and the equivalent substance, wherein the equivalent substance is immobilized on the solid phase by binding between the equivalent substance and a carrier substance which does not bind to the labeled antibody, and binding between the carrier substance and a specific binding substance which specifically binds to the carrier substance and is immobilized on the solid phase.

The present invention is also an immunological assay reagent for measuring an analyte substance in a sample, comprising;

an equivalent substance which is immunologically equivalent to the analyte substance and immobilized on a solid phase during the execution of the measurement; and a labeled antibody which specifically binds to the analyte substance and the equivalent substance, wherein the equivalent substance is immobilized on the solid phase by binding between the equivalent substance and a carrier substance which does not bind to the labeled antibody, and binding between the carrier substance and a specific binding substance which specifically binds to the carrier substance and is immobilized on the solid phase.

The present invention is a method for manufacturing an immunological assay reagent for measuring an analyte substance in a sample, including an equivalent substance which is immunologically equivalent to the analyte substance and immobilized on a solid phase during the execution of the measurement; and a labeled antibody which specifically binds to the analyte substance and the equivalent substance, in which the equivalent substance being immobilized on the solid phase by binding between the equivalent substance and a carrier substance which does not bind to the labeled antibody, and binding between the carrier substance and a specific binding substance which specifically binds to the carrier substance and is immobilized on the solid phase, the method comprising:

freezing the solid phase with the specific binding substance immobilized thereon in a container;

adding a conjugate of the equivalent substance and the carrier substance to the container in which the solid phase is frozen, and further freezing; and freeze-drying a mixture of the frozen solid phase and the frozen conjugate of the equivalent substance and the carrier substance in the container.

Advantageous Effects of Invention

According to the present invention, the reproducibility in the measurement of the analyte substance can be improved.

DESCRIPTION OF EMBODIMENTS

The immunological assay method of the present embodiment will be described below in detail.

A sample in the present embodiment refers to one containing an analyte substance described below. Examples of the sample include: biological samples containing the analyte substance, exemplified by body fluids such as blood, saliva, and urine; environmental water containing the analyte substance from river, lake, sewage or the like; and food containing the analyte substance. Since the assay method of the present embodiment utilizes the reactions in the liquid phase system, more specifically, the sample as used in the present embodiment refers to a liquid containing the analyte substance. When the analyte substance is originally included in non-liquid materials, the sample can be prepared by: suspension in a liquid and others; or extracting the analyte substance by well-known procedures, and dispersing or dissolving it in the liquid. It may be anticipated that an interfering substance which interferes a binding reaction (hereinafter, also referred to as an immunoreaction in this specification) of the labeled antibody to the analyte substance and the equivalent substance may be present in the sample. In this case, the interfering substance present together with the analyte substance is preferably reduced until it does not have any influence on the immunoreaction by removing the interfering substance or purifying the analyte substance prior to the assay method of the present embodiment.

The analyte substance is not particularly limited as long as it has a low molecular weight (preferably, molecular weight of 2000 or less) and specifically binds to the labeled antibody described below. Examples of the analyte substance include amino acids such as homocysteine; vitamins such as folic acid, vitamin $B_{12}$ (cyanocobalamine), and vitamin D (cholecalciferol, calcidiol); proteins such as a thyroid stimulating hormone receptor (TSHR); hormones such as triiodothyronine (T3), thyroxine (T4), 3,5-diiodo-L-thyronine (T2), estrone (E1), estradiol (E2), estriol (E3), progesterone, and cortisol; biopolymers such as carbohydrate chains and lipoids; virus; chemical substances having pharmacological activity; and endocrine disruptors such as bisphenol A.

With respect to the analyte substance as used herein, for example, when homocysteine is an analyte substance, the analyte substance conceptually includes the homocysteine which is measured via its derivatives such as S-adenosylhomocysteine.

The equivalent substance used in the assay method of the present embodiment is a substance that is immunologically equivalent to the analyte substance and immobilized on the solid phase. The "immunologically equivalent" means that it is equal to the analyte substance in reactivity with the labeled antibody described below. More specifically, the equivalent substance refers to a substance which the labeled antibody binds at substantially the same ratio as the analyte substance, when the analyte substance and the equivalent substance are present at the same ratio. For example, when analyte substance is a protein, its partial peptide, its subunit, its derivatives, or others are included as examples of the equivalent substance. Among these, the same kind of substance as the analyte substance, which is prepared in advance (hereinafter, may be expressed as "artificially prepared"), for example, by being extracted from the same material as the sample, is particularly preferably used as the equivalent substance. For example, when homocysteine is converted into S-adenosylhomocysteine and the assay method of the present embodiment is applied with the S-adenosylhomocysteine as the analyte substance, artificially prepared S-adenosylhomocysteine is particularly preferably used as the equivalent substance. When the analyte substance is folic acid, artificially prepared folic acid is particularly preferably used as the equivalent substance.

The solid phase on which the equivalent substance is immobilized is not particularly limited as long as having insolubility to the liquid phase which can be separated by a B/F (bound/free) separation procedure generally carried out in the immunological assay method. The solid phase can be made from, for example, natural materials such as agarose and dextran, synthetic polymer materials such as polyethylene and polystyrene, metal materials, and other various water-insoluble materials. The solid phase can be in a particle form, a rod form, or a plate (sheet) form. Also, for example, the inner wall of the container for carrying out the assay method of the present embodiment can be utilized as the solid phase. Among these, a spherical solid phase which can provide a relatively large surface area is preferable because a large amount of a specific binding substance described below can bind thereto. Although the size of the solid phase is not particularly limited, it is preferable to use a small solid phase in order to improve the reactivity with the analyte substance and shorten the time required for the binding reaction of the labeled antibody to the analyte substance and the equivalent substance. Particularly preferably, the solid phase is in the form of fine particles having a particle diameter (particle diameter at an integrated value of 50% in the particle diameter distribution obtained by the laser diffraction/scattering method or other methods) of about 0.3 μm to 10 μm. The solid phase may enclose a magnetic substance for stirring by magnetic force or a B/F separation procedure.

In the present embodiment, in order to immobilize the above-described equivalent substance to the solid phase, both are not directly bound to each other via chemical bonding or physical adsorption. Specifically, the equivalent substance is bound to the carrier substance, while the specific binding substance which specifically binds to the carrier substance is bound to the solid phase. Then, the binding between the carrier substance and the specific binding substance allows the equivalent substance to indirectly bind to the solid phase. The carrier substance and the specific binding substance can be referred to as immobilizing substances which are substances for immobilizing the equivalent substance to the solid phase. As used herein, the immobilization of the equivalent substance to the solid phase via the carrier substance and the specific binding substance is also referred to as indirect immobilization to the solid phase.

The carrier substance is not particularly limited as long as it does not bind to the labeled antibody described below and can bind to the equivalent substance. Examples of the carrier substance include bovine serum albumin (BSA), avidin, biotin, receptor proteins, fluorescein, and DNA. Among these, fluorescein or BSA which is easily available and cheap can be exemplified as suitable carrier substances. The carrier substance preferably binds to the equivalent substance via chemical bonding. The reason is that the binding sites of the carrier substance and the equivalent substance can be artificially controlled. Note that the carrier substance does not need to be a single and uniform molecule and may be a mixture of two or more kinds thereof.

The specific binding substance is not particularly limited as long as it can specifically bind to the carrier substance, and biotin for avidin, receptors for hormones and the like can be exemplified. Among these, when an antigenic substance such as fluoresceine and BSA is used as the carrier substance, the antibody for the above carrier substance, which is easily manufactured and moreover has sufficient specificity, is preferably used. Note that the specific binding substance does not need to be a single and uniform molecule and may be a mixture of two or more kinds thereof. Further, it is not necessary for the specific binding substance to specifically bind to the carrier substance itself. For example, the carrier substance is fluoresceinated, while a substance (for example, anti-fluorescein antibody) which specifically binds to fluoresceine can be used as the specific binding substance. The solid phase and the specific binding substance bind to each other, for example, by chemical means such as a covalent bond, or by adsorption.

The equivalent substance may be indirectly immobilized on the solid phase in advance before use. Or the sample is subjected to the measurement while the carrier substance is not bound to the specific binding substance, and then the equivalent substance may be indirectly immobilized on the solid phase during the execution of the assay method of the present embodiment. Specifically, the equivalent substance may be immobilized on the solid phase during the reaction in which the analyte substance and the equivalent substance are brought into contact with the labeled antibody in a free state to cause specific binding, or after the reaction in which the analyte substance and the equivalent substance are specifically bound to the labeled antibody.

As used herein, "the equivalent substance is immobilized on the solid phase during the execution of the measurement" conceptually includes the following cases: where the equivalent substance is immobilized on the solid phase before the measurement; where the equivalent substance is immobilized on the solid phase during the reaction in which the analyte substance and the equivalent substance are brought into contact with the labeled antibody in a free state to cause specific binding; and where the equivalent substance is immobilized on the solid phase after the reaction in which the analyte substance and the equivalent substance are specifically bound to the labeled antibody.

In the present embodiment, the labeled antibody is used, in which a labeling substance producing a detectable signal is bound to the antibody which specifically binds to the analyte substance and the equivalent substance. As described above, when the analyte substance itself is used as the equivalent substance, the labeled antibody can be easily prepared by using the analyte substance as immunogen. Further, the labeled antibody may be a mixture of two or more kinds thereof or may be a single and uniform antibody, and a polyclonal antibody or a monoclonal antibody can be used. Among these, a monoclonal antibody is particularly preferable. The reason are that the manufacturing method itself is already established; a desired amount of antibody can be obtained only by culturing a hybridoma, an antibody-forming cell, once the hybridoma is established; and also the reactivity is uniform.

The labeling substance producing a signal is a substance that can be detected by, for example, optical detection or radioactive detection of itself, or can be, for example, optically detected by acting on other substance(s). Specific examples of the labeling substance may include enzymes, chemiluminescent substances, bioluminescent substances, radioisotopes, and color substances. The binding between the labeling substance and the antibody can be formed, for example, by chemical means such as a covalent bond, or by physical binding between affinity substances bound to the both. In the present embodiment, the labeling substance and the antibody can be bound to each other in advance and used as the labeled antibody, or both can also be bound to each other by the binding of affinity substances such as avidin-biotin while the present embodiment is carried out.

When the analyte substance, the equivalent substance, and the labeled antibody which are described above are mixed, the analyte substance and the equivalent substance competitively bind to the labeled antibody. If the analyte substance derived from the sample is present in a large amount, the amount of the equivalent substance bound to the labeled antibody is relatively reduced. Since the equivalent substance is indirectly bound to the solid phase at the end, the B/F separation procedure is carried out after the immunoreaction for a certain period of time, and then a signal depending on the amount of the labeling substance present in the liquid phase, or depending on the amount of the labeling substance forming a complex with the solid phase is measured. The measurement of the signal enables, for example, detection of the analyte substance, or measurement of the amount, the concentration, and others of the analyte substance in the sample. In the present embodiment, preferably, the analyte substance, the equivalent substance, and the labeled antibody are brought into contact with each other in a free state (without the equivalent substance bound to the carrier substance being bound to the solid phase) to cause the immunoreaction. Preferably, during this process, or after their immunoreaction, the carrier substance bound to the equivalent substance is bound to the specific binding substance bound to the solid phase, thereby immobilizing the equivalent substance on the solid phase. This allows the analyte substance, the equivalent substance, and the labeled antibody to react with each other quickly and can improve the reproducibility of the measured value as a result. In order to carry out such measurement, the following processes can be exemplified: first supplying only the analyte substance, the equivalent substance and the labeled antibody to a reaction container; and subsequently supplying the solid phase with the specific binding substance bound thereto.

In addition, the assay method can be exemplified, in which a reagent prepared by freezing the equivalent substance and the solid phase without being bound to each other, more preferably a reagent prepared by freeze-drying after the freezing is used as an assay reagent; a sample including the analyte substance is supplied to dissolve a dried product; and thus the reaction between the analyte substance, the equivalent substance, and the labeled antibody coincides with the reaction between the equivalent substance and the solid phase.

The reagent prepared by freeze-drying after the freezing can be manufactured by: for example, freezing the solid phase with the specific binding substance immobilized thereon in the container; adding a conjugate of the equivalent substance and the carrier substance to the container in which the solid phase is frozen, and further freezing it; and subsequently freeze-drying a mixture of the frozen solid phase and the frozen conjugate of the equivalent substance and the carrier substance in the container.

The amount, the ratio, and others of the components included in the reagent can be appropriately set according to the type of a target sample and others.

According to the present embodiment, the analyte substance in the sample can be reproducibly measured. Therefore, the present embodiment provides the assay method, the reagent, and the manufacturing method therefor which enable the measurement of, for example, the analyte substance in a low concentration with good reproducibility and good accuracy.

Also, in the present embodiment, in order to bind the equivalent substance to the surface of the solid phase, the carrier substance is not directly bound to the solid phase, but bound to the solid phase via the specific binding substance. As a result, this reduces the contact area of the carrier substance on the surface of the solid phase and enables binding of more equivalent substances. Such binding of the equivalent substances allows the equivalent substance to bind to the solid phase while being involved in the immunoreaction. In this way, according to the present embodiment, the effect associated with the above reproducibility is achieved and furthermore the amount of the equivalent substance required for the measurement can be also reduced.

The present embodiment is effective particularly for the case where, for example, the analyte substance is S-adenosylhomocysteine or folic acid, in which only binding of the equivalent substance to the carrier substance causes a problem of difficulty in uniformly immobilizing the equivalent substance to the surface of the solid phase. Application of the present embodiment, for example, can uniform the amount of S-adenosylhomocysteine (or folic acid) bound to the surface of the solid phase and avoid variation of the measured results associated with variation of the bound amount, thereby achieving good reproducibility. Conventionally, in order to avoid this problem, S-adenosylhomocysteine (or folic acid) more than necessary has been consumed to control the amount of S-adenosylhomocysteine (or folic acid) bound to the surface of the solid phase, and moreover complicated steps for quality control have been required in preparation of the solid phase, which can be skipped in the present embodiment.

EXAMPLE

Hereinafter, although the present invention will be further described by way of Examples of homocysteine, an example of amino acids, and folic acid, an example of vitamins, the present invention is not limited thereto. In the following description, a fluoresceinated S-adenosylhomocysteine solution may be expressed as a solution (A), beads with anti-fluorescein antibodies immobilized thereon as beads (B), an ALP-labeled anti-S-adenosylhomocysteine antibody solution as a solution (C), beads with S-adenosylhomocysteine directly immobilized thereon as beads (D), a fluoresceinated folic acid solution as a solution (E), an ALP-labeled anti-folic acid antibody solution as a solution (F), and beads with folic acid directly immobilized thereon as beads (G).

Example 1: Assay Reagent for Homocysteine, Manufacture Thereof, and Measurement Using Same (1) Preparation of Fluoresceinated S-adenosylhomocysteine Solution Zero point five mg of a conjugate (SAH-BSA) of commercially available S-(5'-adenosyl)-L-homocysteine (produced by Sigma-Aldrich Corporation) (hereinafter, referred to as S-adenosylhomocysteine or SAH) and bovine serum albumin (BSA) was dissolved in 0.25 mL of borate buffer (50 mmol/L, pH 9.0). Five equivalents of 6-(Fluorescein-5-carboxamide) hexanoic acid succinimidyl ester (5-SFX) dissolved in N,N-dimethylformamide was added thereto and allowed to react at 37° C. for 3 hours to make fluoresceinated S-adenosylhomocysteine. This was diluted with 0.1 mol/L Tris buffer (pH 7.5) including BSA to produce a fluoresceinated S-adenosylhomocysteine solution (A). S-adenosylhomocysteine in the solution (A) specifically reacts with the solution (C) prepared below and its reactivity was equal to that of S-adenosylhomocysteine which was obtained by treating a blood sample. BSA in the solution (A) did not react with the solution (C) prepared below.

(2) Preparation of Solid Phase with Anti-Fluorescein Antibody Immobilized Thereon Spherical plastic beads having a diameter of about 2 mm were used as a solid phase. Per plastic bead, 0.1 μg of anti-fluorescein antibodies which specifically bind to fluorescein were added and incubated at 30° C. for 17 hours, allowing the antibodies to be adsorbed to the beads. The washed beads were placed in a 1% BSA solution controlled at 53° C. for 3 hours for blocking and thus beads (B) with anti-fluorescein antibodies immobilized thereon were obtained.

(3) Preparation of Labeled Antibody Solution for Detection

A mouse was immunized with commercially available S-adenosylhomocysteine as an antigen to prepare anti-S-adenosylhomocysteine antibodies which specifically bind to S-adenosylhomocysteine. The prepared antibodies were bound to alkaline phosphatase (ALP), which were then diluted with 0.1 mol/L Tris buffer (pH 7.5) including BSA to produce an ALP-labeled anti-S-adenosylhomocysteine antibody solution (C).

(4) Measurement of Standard Solution

Commercially available S-adenosylhomocysteine was diluted with 0.1 mol/L Tris buffer (pH 7.5) to prepare standard solutions for homocysteine measurement of the concentrations shown in Table 1. The buffer without S-adenosylhomocysteine was used as a standard solution of zero concentration. The solution (A), the standard solution, and the solution (C) were added to the beads (B), and the mixture was set in a commercially available immunological assay analyzer (trade name: AIA-600II, manufactured by Tosoh Corporation) and allowed to react at 37° C. for 10 minutes. After a B/F separation procedure, 4-methylumbelliferyl phosphate (4MUP), a substrate of ALP, was added thereto, and the increasing rate (nmol/L/second) of 4-methylumbelliferone (4MU), which was produced by decomposition of 4MUP by ALP, was calculated by measuring the fluorescence intensity of 4MU. About 0.08 µg of the solution (A) was used per reaction.

The results are shown in Table 1. The results in Table 1 represent the mean values obtained by repeating the same procedure 5 times for the standard solution of each concentration.

(5) Measurement of Blood Sample

A reducing agent, an enzyme for adding adenosine, and adenosine were added to a blood sample taken from a healthy person with his/her consent, and the mixture was incubated at 37° C. for 10 minutes to convert homocysteine in the sample into S-adenosylhomocysteine, followed by the immunological assay. The solution (A), the treated sample, and the solution (C) were added to the beads (B), which was set in the commercially available immunological assay analyzer and allowed to react at 37° C. for 10 minutes. After a B/F separation procedure, 4MUP was added thereto and the increasing rate (nmol/L/second) of 4MU was calculated by measuring the fluorescence intensity of 4MU.

The results are shown in Table 1. The results in Table 1 represent the mean values obtained by repeating the same procedure 5 times. The concentrations of the samples in the table are the values measured by the HPLC method.

Comparative Example 1

(1) Preparation of Solid Phase with Equivalent Substance Directly Immobilized Thereon Per spherical plastic bead having a diameter of about 2 mm, 0.01 µg of the SAH-BSA and 0.2 µg of BSA were added and incubated at 30° C. for 17 hours, allowing S-adenosylhomocysteine to be adsorbed to the beads. The washed beads were placed in a 0.1% blocking agent (trade name: Block Ace, produced by DS Pharma Biomedical Co., Ltd.) solution controlled at 53° C. for 3 hours for blocking and thus beads (D) with S-adenosylhomocysteine directly immobilized thereon were obtained.

(2) Measurement of Standard Solution

The same standard solution as that in Example 1 and the solution (C) were added to the beads (D), which was set in the commercially available immunological assay analyzer and allowed to react at 37° C. for 10 minutes. After a B/F separation procedure, 4MUP was added thereto and the increasing rate (nmol/L/second) of 4MU was calculated by measuring the fluorescence intensity of 4MU. About 0.12 µg of the SAH-BSA was used per reaction.

The results are shown in Table 1. The results in Table 1 represent the mean values obtained by repeating the same procedure 5 times for the standard solution of each concentration.

(3) Measurement of Blood Sample

A sample treated as described in Example 1 (5) and the solution (C) were added to the beads (D), which was set in the commercially available immunological assay analyzer and allowed to react at 37° C. for 10 minutes. After a B/F separation procedure, 4MUP was added thereto and the increasing rate (nmol/L/second) of 4MU was calculated by measuring the fluorescence intensity of 4MU.

The results are shown in Table 1. The results in Table 1 represent the mean values obtained by repeating the same procedure 5 times.

TABLE 1

| | Solid Phase | | | |
| --- | --- | --- | --- | --- |
| | Example 1 | | Comparative Example 1 | |
| | Mean Value of Increasing Rate of Fluorescence Intensity (mean) nmol/L/s | Coefficient of Variation (CV) % | Mean Value of Increasing Rate of Fluorescence Intensity (mean) nmol/L/s | Coefficient of Variation (CV) % |
| Concentration of Standard Solution µmol/L | | | | |
| 0 | 30.62 | 0.97 | 33.16 | 2.66 |
| 2.10 | 20.50 | 1.38 | 22.54 | 3.03 |
| 4.12 | 15.43 | 1.74 | 16.62 | 2.35 |
| 8.14 | 10.06 | 1.29 | 10.66 | 4.78 |
| 15.1 | 6.217 | 2.37 | 6.972 | 3.62 |
| 50.2 | 2.498 | 1.69 | 2.955 | 3.40 |
| Concentration of Sample µmol/L | | | | |
| 9.9 | 9.641 | 2.78 | 10.18 | 14.3 |
| 11.7 | 8.435 | 5.18 | 8.759 | 3.34 |
| 24.9 | 4.640 | 5.93 | 5.168 | 9.52 |
| 13.5 | 7.144 | 8.80 | 7.911 | 9.60 |
| 7.0 | 11.68 | 2.37 | 12.17 | 1.62 |

CV: Standard Deviation of Increasing Rate/mean × 100

Table 1 shows that the coefficients of variation of the measured results for the standard solution in Example 1, in which the assay method of the present embodiment was carried out, are smaller than those in the method of Comparative Example 1, and thus, the reproducibility of repetitive measurements is improved. For the sample, although the coefficients of variation of some measured results in Example 1 are larger than those in the method of Comparative Example 1, there is no sample with more than 10% of coefficient of variation. Accordingly, it is said that the reproducibility of the assay method of the present embodiment is improved in total. This indicates that the equivalent substance is uniformly immobilized on the entire surface of the solid phase in the method of the present embodiment, in which the equivalent substance is bound to the solid phase via the specific binding substance such as an antibody. In addition, the amount of the equivalent substance used per measurement in the method of the present embodiment is about two thirds of the amount used in the immobilization method without anti-fluorescein antibodies, which shows that even small amount of the equivalent substance can cause the immunoreaction efficiently.

Example 2: Freeze-Dried Assay Reagent for Homocysteine, Manufacture Thereof, and Measurement Using Same (1) Manufacture of Freeze-Dried Reagent First, the beads (B) and the solution (C) were placed in a plastic container and frozen. Subsequently, the solution (A) was further added thereto and frozen. The obtained frozen reagent was dried thereby to manufacture a reagent (freeze-dried product) for homocysteine measurement.

(2) Measurement

The standard solution of zero concentration was added to the freeze-dried reagent manufactured as described above. The increasing rate (nmol/L/second) of 4MU, which was produced by decomposition of 4MUP by ALP, was calculated by measuring the fluorescence intensity of 4MU with the commercially available immunological assay analyzer as in Example 1.

The results are shown in Table 2. The results in Table 2 represent the mean values obtained by repeating the same procedure 5 times.

Example 3

(1) Manufacture of Freeze-Dried Reagent

First, the solution (A) and the beads (B) were placed in a plastic container and bound to each other, which was then frozen. Subsequently, the solution (C) was further added thereto and frozen. The obtained frozen reagent was dried thereby to manufacture a reagent (freeze-dried product) for homocysteine measurement.

(2) Measurement

The standard solution of zero concentration was added to the freeze-dried reagent manufactured as described above. The increasing rate (nmol/L/second) of 4MU, which was produced by decomposition of 4MUP by ALP, was calculated by measuring the fluorescence intensity of 4MU with the commercially available immunological assay analyzer as described above.

The results are shown in Table 2. The results in Table 2 represent the mean values obtained by repeating the same procedure 5 times.

TABLE 2

| Solid Phase | Increasing Rate of Fluorescence Intensity nmol/L/s | | | | | Mean of Increasing Rate (mean) nmol/L/s | Standard Deviation (SD) — | Coefficient of Variation (CV) % |
|---|---|---|---|---|---|---|---|---|
| Example 2 | 34.87 | 36.21 | 31.66 | 32.10 | 34.32 | 33.83 | 1.915 | 5.66 |
| Example 3 | 33.27 | 40.68 | 36.94 | 32.12 | 34.15 | 35.43 | 3.430 | 9.68 |

Table 2 shows that in the case such as Example 2 in which the reagent is manufactured by the manufacturing method where the equivalent substance is not immobilized on the solid phase in a manufacturing stage of the reagent and the equivalent substance is immobilized to the solid phase during the measurement, the coefficients of variation of the measured results are smaller than those in the method of Example 3 where the equivalent substance is bound to the solid phase in advance and subsequently freeze-dried, and thus, the reproducibility of repetitive measurements is improved. This indicates that when the equivalent substance is in a free state without being immobilized on the solid phase at the time when the immunoreaction is initiated by addition of the sample (in the case of Examples 2 and 3, the standard solution of zero concentration) to the freeze-dried reagent, the reaction between the labeled antibody and the analyte substance and the reaction between the labeled antibody and the equivalent substance are accelerated.

Example 4: Immunoreaction Reagent for Folic Acid, Manufacture Thereof, and Measurement Using Same (1) Preparation of Fluoresceinated Folic Acid Solution Ten mg of a conjugate (BSA-FOL) of commercially available folic acid (produced by Wako Pure Chemical Industries, Ltd.) and bovine serum albumin were dissolved in 4.4 mL of borate buffer (50 mmol/L, pH 9.0). Five equivalents of 5-SFX dissolved in N,N-dimethylformamide was added thereto, which was allowed to react at 37° C. for 3 hours to make fluoresceinated folic acid. This was diluted with 0.05 mol/L Tris buffer (pH 7.5) including BSA to produce a fluoresceinated folic acid solution (E).

(2) Preparation of Labeled Antibody Solution for Detection

A mouse was immunized with commercially available folic acid as an antigen to prepare anti-folic acid antibodies which specifically bind to folic acid. The prepared antibodies were bound to ALP, which were then diluted with 0.05 mol/L Tris buffer (pH 7.5) including BSA to produce an ALP-labeled anti-folic acid antibody solution (F).

(3) Measurement of Standard Solution

Commercially available folic acid (produced by Wako Pure Chemical Industries, Ltd.) was diluted with 0.01 mol/L phosphate buffer (pH 7.5) to prepare standard solutions for folic acid measurement of the concentrations shown in Table 3. The buffer without folic acid was used as a standard solution of zero concentration. The solution (E), the standard solution, and the solution (F) were added to the beads (B), which was set in the commercially available immunological assay analyzer and allowed to react at 37° C. for 40 minutes. After a B/F separation procedure, 4MUP was added thereto and the increasing rate (nmol/L/second) of 4MU was calculated by measuring the fluorescence intensity of 4MU. The results are shown in Table 3. The results in Table 3 represent the mean values obtained by repeating the same procedure 3 times for the standard solution of each concentration.

(4) Measurement of Blood Sample

A reducing agent was added to a blood sample taken from a healthy person with his/her consent, and the mixture was incubated at 37° C. for 10 minutes to release folic acid from a folate-binding protein in the sample, followed by the immunoreaction. The solution (E), the treated sample, and the solution (F) were added to the beads (B), which was set in the commercially available immunological assay analyzer and allowed to react at 37° C. for 40 minutes. After a B/F separation procedure, 4MUP was added thereto and the increasing rate (nmol/L/second) of 4MU was calculated by measuring the fluorescence intensity of 4MU.

The results are shown in Table 3. The results in Table 3 represent the mean values obtained by repeating the same procedure 3 times. The concentrations of the samples in the table are the values measured by AIA-PACK FOLATE (produced by Tosoh Corporation) and the commercially available immunological assay analyzer (AIA-600II, manufactured by Tosoh Corporation).

Comparative Example 2

(1) Preparation of Solid Phase with Folic Acid Directly Immobilized Thereon

Per spherical plastic bead having a diameter of about 2 mm, 0.03 µg of BSA-FOL and 0.2 µg of BSA were added and incubated at 30° C. for 17 hours, allowing folic acid to be adsorbed to the beads. The washed beads were placed in a 0.1% blocking agent (trade name: Block Ace, produced by DS Pharma Biomedical Co., Ltd.) solution controlled at 53° C. for 3 hours for blocking and thus beads (G) with folic acid immobilized thereon were obtained.

(2) Measurement of Standard Solution

The same standard solution as that in Example 3 and the solution (F) were added to the beads (G), and the mixture was set in the commercially available immunological assay analyzer and allowed to react at 37° C. for 40 minutes. After a B/F separation procedure, 4MUP was added thereto and the increasing rate (nmol/L/second) of 4MU, which was produced by decomposition of 4MUP by ALP, was calculated by measuring the fluorescence intensity of 4MU.

The results are shown in Table 3. The results in Table 3 represent the mean values obtained by repeating the same procedure 3 times for the standard solution of each concentration.

(3) Measurement of Blood Sample

A sample treated as described in Example 3 (4) and the solution (F) were added to the beads (G), and the mixture was set in the commercially available immunological assay analyzer and allowed to react at 37° C. for 40 minutes. After a B/F separation procedure, 4MUP was added thereto and the increasing rate (nmol/L/second) of 4MU was calculated by measuring the fluorescence intensity of 4MU.

The results are shown in Table 3. The results in Table 3 represent the mean values obtained by repeating the same procedure 3 times.

TABLE 3

| | Solid Phase | | | |
| --- | --- | --- | --- | --- |
| | Example 4 | | Comparative Example 2 | |
| | Mean Value of Increasing Rate of Fluorescence Intensity (mean) nmol/L/s | Coefficient of Variation (CV) % | Mean Value of Increasing Rate of Fluorescence Intensity (mean) nmol/L/s | Coefficient of Variation (CV) % |
| Concentration of Standard Solution ng/mL | | | | |
| 0 | 65.36 | 0.457 | 41.94 | 33.5 |
| 1.29 | 49.84 | 1.76 | 31.22 | 88.7 |
| 3.18 | 37.08 | 1.23 | 20.47 | 71.7 |
| 6.51 | 23.63 | 1.37 | 42.44 | 20.3 |
| 13.1 | 15.43 | 0.499 | 27.92 | 15.8 |
| 25.7 | 8.568 | 1.05 | 28.06 | 51.0 |
| Concentration of Sample ng/mL | | | | |
| 1.80 | 45.29 | 0.579 | 17.09 | 90.4 |
| 2.15 | 39.85 | 2.15 | 28.20 | 44.4 |
| 3.46 | 37.86 | 0.700 | 23.30 | 48.7 |
| 6.60 | 25.10 | 1.01 | 11.53 | 40.1 |
| 15.5 | 11.02 | 1.92 | 21.39 | 25.4 |

CV: Standard Deviation of Increasing Rate/mean × 100

Table 3 shows that the competitive reaction of folic acid occurs in the standard solutions and the samples and the increasing rate of the fluorescence intensity of 4MU depends on the concentration of folic acid in Example 3. The coefficients of variation also fall within the acceptable range of this measurement system. This indicates that in the method of the present embodiment where the equivalent substance is bound to the solid phase via the specific binding substance (antibody), the equivalent substance is uniformly immobilized on the entire surface of the solid phase and involved in the immunoreaction. On the other hand, in Comparative Example 2 where the equivalent substance is bound to the carrier substance and this carrier substance is directly bound to the solid phase, the competitive reaction does not occur. Thus, it was found that Comparative Example 2 was not applicable to the measurement of folic acid in the sample.

The invention claimed is:

1. An immunological assay method, comprising
measuring an analyte substance in a sample by using: an equivalent substance which is immunologically equivalent to the analyte substance and immobilized on a solid phase during the execution of the measurement; and a labeled antibody which specifically binds to the analyte substance and the equivalent substance,
wherein the equivalent substance is immobilized on the solid phase by binding between the equivalent substance and a carrier substance which does not bind to the labeled antibody, and binding between the carrier substance and a specific binding substance which specifically binds to the carrier substance and is immobilized on the solid phase,
wherein the carrier substance is fluorescein or bovine serum albumin,
wherein the analyte substance and the equivalent substance are selected from (a) and (b):
wherein in (a), the analyte substance is S-adenosylhomocysteine which is derived from a blood component, and the equivalent substance is artificially prepared S-adenosylhomocysteine; and
wherein in (b), the analyte substance is folic acid which is derived from a blood component, and the equivalent substance is artificially prepared folic acid.

2. The assay method according to claim 1, wherein the equivalent substance is immobilized on the solid phase during a process in which the analyte substance and the equivalent substance are brought into contact with the labeled antibody in a free state to cause binding, or after the analyte substance and the equivalent substance are bound to the labeled antibody.

3. An immunological assay reagent for measuring an analyte substance in a sample, comprising:
an equivalent substance which is immunologically equivalent to the analyte substance and immobilized on a solid phase during the execution of the measurement; and
a labeled antibody which specifically binds to the analyte substance and the equivalent substance,
wherein the equivalent substance is immobilized on the solid phase by binding between the equivalent substance and a carrier substance which does not bind to the labeled antibody, and binding between the carrier substance and a specific binding substance which specifically binds to the carrier substance and is immobilized on the solid phase,
wherein the carrier substance is fluorescein or bovine serum albumin,
wherein the analyte substance and the equivalent substance are selected from (a) and (b):
wherein in (a), the analyte substance is S-adenosylhomocysteine which is derived from a blood component, and the equivalent substance is artificially prepared S-adenosylhomocysteine; and
wherein in (b), the analyte substance is folic acid which is derived from a blood component, and the equivalent substance is artificially prepared folic acid.

4. The immunological assay reagent according to claim 3, wherein said labeled antibody is labeled with a substance that can be detected by optical detection.

5. The immunological assay reagent according to claim 3, wherein said labeled antibody is labeled with a substance that can be detected by radioactive detection.

6. The immunological assay reagent according to claim 3, wherein said labeled antibody is labeled with alkaline phosphatase.

* * * * *